United States Patent
Missbichler et al.

(10) Patent No.: US 9,364,437 B2
(45) Date of Patent: Jun. 14, 2016

(54) DIAMINOOXIDASE-CONTAINING PHARMACEUTICAL COMPOSITIONS

(71) Applicant: SCIOTEC DIAGNOSTIC TECHNOLOGIES GMBH, Tulln (AT)

(72) Inventors: Albert Missbichler, Vienna (AT); Franz Gabor, Gerersdorf (AT); Herwig Reichl, Ilz (AT)

(73) Assignee: SCIOTEC DIAGNOSTIC TECHNOLOGIES GMBH, Tullin (AT)

(*) Notice: Subject to any disclaimer, the term of this patent is extended or adjusted under 35 U.S.C. 154(b) by 125 days.

(21) Appl. No.: 14/245,358

(22) Filed: Apr. 4, 2014

(65) Prior Publication Data
US 2014/0220148 A1 Aug. 7, 2014

Related U.S. Application Data

(62) Division of application No. 12/862,379, filed on Aug. 24, 2010, now Pat. No. 8,716,244, which is a division of application No. 11/571,732, filed as application No. PCT/EP2005/053234 on Jul. 6, 2005, now abandoned.

(30) Foreign Application Priority Data

Jul. 7, 2004 (AT) ................ A 1150/2004

(51) Int. Cl.
| *A61K 38/44* | (2006.01) |
| *A61K 9/16* | (2006.01) |
| *A23L 1/03* | (2006.01) |
| *A23L 1/0534* | (2006.01) |
| *A23L 1/30* | (2006.01) |
| *A61K 9/06* | (2006.01) |
| *A61K 9/50* | (2006.01) |
| *A23L 1/305* | (2006.01) |

(52) U.S. Cl.
CPC . *A61K 9/16* (2013.01); *A23L 1/034* (2013.01); *A23L 1/0534* (2013.01); *A23L 1/30* (2013.01); *A23L 1/3053* (2013.01); *A61K 9/06* (2013.01); *A61K 9/1623* (2013.01); *A61K 9/1652* (2013.01); *A61K 9/50* (2013.01); *A61K 38/44* (2013.01); *A61K 38/443* (2013.01); *C12Y 104/03006* (2013.01)

(58) Field of Classification Search
None
See application file for complete search history.

(56) References Cited

U.S. PATENT DOCUMENTS

| 3,639,579 A | 2/1972 | Urbin ............................. 424/94 |
| 3,721,733 A | 3/1973 | van Leeuwen ................. 424/94 |
| 4,652,449 A | 3/1987 | Ropars et al. ................. 424/533 |
| 4,725,540 A | 2/1988 | Underberg et al. ............. 435/42 |
| 5,270,033 A | 12/1993 | Montgomery ................. 424/50 |
| 2004/0115189 A1 | 6/2004 | Mondovi et al. ........... 424/94.63 |

FOREIGN PATENT DOCUMENTS

| DE | 10239029 | 3/2004 |
| EP | 0132674 | 2/1985 |
| FR | 2101095 | 2/1974 |
| FR | 2215944 | 7/1976 |
| GB | 479487 | 2/1938 |
| JP | 2002-16050 | 6/2002 |
| JP | 2002-531394 | 9/2002 |
| JP | 2003-212773 | 7/2003 |
| JP | 2004-167178 | 6/2004 |
| WO | WO 02/43745 | 6/2002 |
| WO | WO 02/066669 | 8/2002 |
| WO | WO 2004/017931 | 3/2004 |

OTHER PUBLICATIONS

"Tablet," The American Heritage Medical Dictionary, 2007, retrieved from http://www.credoreference.com/entry/hmmedicaldict/tablet, retrieved on May 19, 2010.
Atkinson et al., "The effect of histamine on the gastric secretory response to histamine," *American Journal of Physiology*, 132:51-56, 1941 (abstract only).
Hajos, "About the treatment of allergic respiratory diseases (Histamine, histaminase, histamine-azoprotein, antihistamines)," *Orc. Hetil.*, 141:859-861, 2000.
Janes et al., "A new redox cofactor in eukaryotic enzymes: 6-hydroxydopa at the active site of bovine serum amine oxidase," *Science*, 248:981-987, 1990.
Janes et al., "Identification of topaquinone and its consensus sequence in copper amine oxidases," *Biochemistry*, 31:12147-12154, 1992.
Jian and Yongfang, "Quinoprotein—Purification and characterization of diamine oxidase from pig kidney," Wuhan Univ. (*Natural Science Edition*), 42:507-512, 1996 (English Abstract).
Kitanaka et al., "Expression of diamine oxidase (histaminase) in guinea-pig tissues," *European J. Pharm.*, 437:179-185, 2002.
Kluetz and Schmidt, "Diamine oxidase: molecular weight and subunit analysis," *Biochem. Biophys.*, 76:40-45, 1997.
Küfner et al., "Determination of histamine degradation capacity in extremely small human colon samples," *Inflamm. res* 50, Supplement 2:S96-S97, 2001.
Maintz and Novak, "Histamine and histamine intolerance," *Am J Clin Nutr.*, 85:1185-1196, 2007.
Mu et al., "Tyrosine codon corresponds to topa quinone at the active site of copper amine oxidases," *J. Biol. Chem.*, 267:7979-7982, 1992.
Nilsson et al., "Inhibition of diamine oxidase promotes uptake of putrescine from rat small intestine," *Inflammation Res.*, 45:513-518, 1996.
Office Action, issued in Chinese Application No. 200580022791, dated Feb. 9, 2009.
Office Action, issued in U.S. Appl. No. 11/571,732, mailed May 13, 2009.

(Continued)

*Primary Examiner* — Savitha Rao
*Assistant Examiner* — Gregg Polansky
(74) *Attorney, Agent, or Firm* — Norton Rose Fulbright US LLP

(57) ABSTRACT

The present invention relates to pharmaceutical compositions, food supplement compositions and cosmetic compositions comprising diaminooxidase, and to the use thereof.

18 Claims, No Drawings

(56) References Cited

OTHER PUBLICATIONS

Office Action, issued in U.S. Appl. No. 11/571,732, mailed Sep. 29, 2009.
Office Action, issued in U.S. Appl. No. 11/571,732, mailed May 24, 2010.
Rinaldi et al., "Diamine oxidase from pig kidney: new purification method and amino acid composition," *Prep. Biochem.*, 12:11-28, 1982.
Scarabelli et al., "The hematic histamina in malignant tumors of alimentary canal and respiratory apparatus," *Chir. Ital.*, 31:789-795, 1979.
Shah and Ali, "The glycoprotein nature of pig kidney diamine oxidase," *Biochem. J.*, 253:103-107, 1988.
Szojkowits et al., "Histaminase and its clinical significance," *Wiad. Lek.*, 40:686-690, 1987, English Abstract.
Taylor, "Histamine food poisoning: toxicology and clinical aspects," *Crit. Rev. Toxicol.*, 17:91-128, 1996.
Wöhrl et al., "Histamine intolerance-like symptoms in healthy volunteers after oral provocation with liquid histamine," *Allergy Asthma Proc.*, 25(5):305-311, 2004.
Floris et al., "Purification of pig kidney diamine oxidase by gel-exclusion chromatography," *FEBS Letters*, 72(1):179-181, 1976.
Raithel et al., "The analysis and topographical distribution of gut diamine oxidase activity in patients with food allergy", *Annals of the New York Academy of Science*, 859:258-261, 1998.
Raithel et al., "The involvement of the histamine degradation pathway by Diamine oxidase in manifest gastrointestinal allergies", *Inflammation Research*, 48. p. 75-S76, 1999.
Rruijnzeel-Koomen et al., "Adverse reactions to food", *Allergy*, 50(8):623-635, 1995.
Mayer et al., "Highly Sensitive Determination of DAO Activity by Oxidation of a Luminescence Reagent", *Appl. Biochem. Biotechnol.*, 143(2):164-175, 2007.

DIAMINOOXIDASE-CONTAINING PHARMACEUTICAL COMPOSITIONS

CROSS REFERENCE TO RELATED APPLICATIONS

This application is a divisional application of U.S. patent application Ser. No. 12/862,379 filed on Aug. 24, 2010, which is a divisional of U.S. patent application Ser. No. 11/571,732 filed on 13 Nov. 2007, which is a national phase application under 35 U.S.C. §371 of International Application No. PCT/EP2005/053234 filed 6 Jul. 2005, which claims priority to Austrian Patent Application No. A 1150/2004 filed 7 Jul. 2004. The entire text of each of the above-referenced disclosures is specifically incorporated herein by reference.

The present invention relates to compositions for the treatment and/or prevention of histamine-induced diseases and conditions.

Histamine (1H-imidazole-4-ethylamine) forms by the enzymatic decarboxylation of histidine and, thus, is a basic biogenic amine having a molecular weight of 111 Da.

In the organism, histamine occurs practically ubiquitously. It is produced by humans themselves and stored in inactive form in the metachromatic granules of the mast cells and basophilic leukocytes, where it is available for an immediate release. The highest histamine concentrations are measured in the lungs. After its release, histamine is a highly potent mediator for a plurality of physiological and pathophysiological processes, often also via an interaction with cytokines.

Moreover, histamine may also get into the body from the outside, by inhaling, on the one hand, or orally, e.g. by ingesting histamine-containing foodstuffs, such as cheese, wine, canned fish and sauerkraut.

The most important functions and effects of histamine in the human and animal body, respectively, are:

1) Dilation of the capillaries, increase in the capillary permeability and drop of blood pressure.
2) Contractions of the smooth muscles, i.a. of the bronchial muscles in the lungs.
3) Induction of an increase gastric acid secretion.
4) Increase in the heart rate.
5) Histamine is the mediator of the allergic immediate type reaction, it is the most important mediator in allergic diseases, such as Rhinitis allergica (hay fever) and Asthma bronchiale.
6) Moreover, histamine is the classical trigger of an urticaria (nettle rash) and it plays an important role in drug allergies or intolerances.

High concentrations of freely circulating histamine initiate undesired effects, such as headaches, stuffy or runny nose, obstruction of the respiratory tract, tachycardia as well as extrasystoles, and furthermore, gastro-intestinal complaints which may lead from loose stools up to diarrhea, and hypotension. Often also swellings of the eyelids, sometimes also urticarial exanthemas have been described. Moreover, reddening of the skin, a drop in blood pressure and bronchospasms may occur. The following table shows the symptoms as a function of the histamine concentration in blood.

| Histamine (ng/ml) | Body reactions |
|---|---|
| 0-1 | none |
| 1-2 | Increase gastric juice secretion |
| 3-5 | Tachycardia, skin irritations |
| 6-8 | Drop in blood pressure |
| 7-12 | Bronchospasm |
| approx. 100 | Cardiac arrest |

In the organism of mammals, histamine is degraded by two enzymes: diaminoxidase (DAO, EC 1.4.3.6) and histamine-N-methyltransferase (NMT, EC 2.1.1.8) (Mizugushi et al., 1994). DAO catalyzes the oxidative deamination of histamine to imidazole acetaldehyde; NMT catalyzes the N-methylation to N-methyl-histamine.

Both degradation pathways are essential to the organism: DAO removes histamine which has, e.g., been taken up in the gastro-intestinal tract via the food, NMT controls the histaminergic signal transmission in the nervous system (Kitanaka et al., 2002).

It is the main objective of DAO to prevent histamine that has been ingested with the food from getting from the intestines into the blood circulation. Failure of this protective mechanism may result in anaphylactic shock in extreme cases (Taylor 1986, Nilsson et al., 1996). DAO is a secretory protein and, thus, acts extracellularily, whereas N-methyl-transferase is exclusively active in the cytosol (Küfner et al., 2001).

Native DAO which can degrade further biogenic amines, such as, e.g., putrescin, spermidin and cadaverine, in addition to histamine, and which may, e.g. be recovered from porcine kidney, is a homodimeric copper-containing glycoprotein, in which the sub-units are connected via disulfide bonds. DAO has a molecular weight of approximately 182 kDa (Kluetz and Schmidt, 1997; Rinaldi et al., 1982) and a carbohydrate portion of approximately 11% (Shah and Ali, 1988). The enzyme belongs to the class of the copper-containing aminooxidases, which catalyze the oxidative deamination of primary amines to aldehydes, ammonia and hydrogen peroxide according to the following general reaction scheme (Bachrach 1985): $RCH_2NH_2 + H_2O + O_2 \rightarrow RCHO + NH_3 + H_2O_2$, the residue R containing an amino group.

Characteristic of the copper-containing amino oxidases is a topaquinone at the active center which forms by post-translational modification of a conserved tyrosine-residue (James et al., 1990, James et al., 1992; Mu et al., 1992).

DAO is mainly found in the small intestines, in the liver, in the kidneys and in blood in white blood cells. In pregnant subjects, DAO is additionally formed in the placenta. Pregnant subjects have a blood-DAO level that is higher by approximately 500 to 1000 times than that of non-pregnant subjects. DAO is continuously produced and excreted into the intestinal lumen. In healthy humans, food rich in histamines therefore is already largely freed from histamine in the intestines. The remaining histamine is degraded when it passes through the intestinal mucosa by the DAO present there. Histamine is decomposed to imidazole-acetaldehyde and, furthermore, to imidazole-acetoacetic acid. The co-factors of DAO are 6-hydroxydopa and presumably pyridoxalphosphate, the vitamin B6. DAO is a sensitive enzyme which can be inhibited by various substances, i.a. by biogenic amines, alcohol and its degradation product acetaldehyde, and various medicaments. In neuronal tissue, so far no DAO activity could be detected.

As has already been mentioned before, exogenous histamine ingested with the food, but also endogenous histamine can trigger a large variety of disorders due to allergic reactions. With regard to its clinical value, at least three forms of a histamine intolerance based on a reduced DAO activity are to be pointed out:

Few people have a congenital DAO deficiency and do not lose it, either.

During an infection of the intestinal mucosa, a transient DAO deficiency may occur. When the infection has been healed, also the DAO activity returns to normal.

When administering various activity-inhibiting substances, there may result exogenously a reduced DAO activity. Among them are primarily alcohol and its degradation product, acetaldehyde, certain foodstuffs rich in amines, and many medicaments.

In all the cases, the symptoms initially described occur more or less strongly and cannot be attributed easily in most instances. A rapid clarification of the functional activity of the enzyme allows for a rapid and simple therapy and for providing an appropriate dietary plan.

A frequent reason for the occurrence of a histamine intolerance is the sensitivity of the enzyme relative to a large number of chemical substances. Many of them occur in different medicaments. The most important DAO inhibitors are acriflavine, diazepam, N-methyl-N-formylhydrazine, b-aminopropionitriles, Dimaprit, O-methylhdroxylamine, agmantine, ethanol (10%), Pargyline, Aldomet, Furosemide, Phenamil, Amiloride, Guanabenz, Phenelzine, Aminoguanidine, Guanfacine, Phenformin, Amitryptiline, guanidine, phenyprazine, amodiaquine, haloperidol, promethiazine, anserine, Hyamine 1622, propranolol, aziridinyl-alkylamines, hydroxychloroquines, B1 pyrimidine, hydroxylamine, quinacrine, Burimamide, Impromidine, semicarbazide, cadaverine, imidazol derivatives, thiamines, Carnosine, iproniazid, thioridazine, chlorothiazide, isocarboxazide, tranylcypramine, chlorpromazine, isoniazide, trimethoprim, cimetidine, metiamide, tryptamine, clonidine, metronidazole, tyramine, cyanide, nazlinin (alkaloid), diamines (also histamine) and Nt-methyl-histamine.

In WO 02/43745 the systemic use of DAO of plant origin for the treatment of histamine-mediate diseases is disclosed. The administration of DAO or of enzymes in general which are directly isolated from plants is a great problem because of the frequent occurrence of allergens in plants, primarily in view of the fact that the leguminous plants disclosed in WO 02/43745 have a high allergenic potential.

It is an object of the present invention to provide compositions for the treatment and prevention of histamine-induced diseases and conditions which do not have the side-effects of products available on the market which mainly comprise cortisone, and which eliminate the disadvantages encountered in the prior art mentioned above. It is a further object of the present invention to increase the concentration of active diaminooxidase within the body, in particular in the intestinal tract, of an individual to thereby assist in, or enable, respectively, the degradation particularly of histamine that has been exogenically supplied (e.g. with the food).

Therefore, the present invention relates to pharmaceutical compositions for the treatment of histamine-induced diseases, comprising diaminooxidase, wherein the composition is provided in an application form for epidermal, oral, peroral or sublingual administration as a hydrogel, gastric-juice-resistant pellet, drops, in particular eye drops and nose drops, or as a tablet, food supplement compositions, or dietary foodstuffs and cosmetic compositions comprising diaminooxidase. In the compositions according to the invention, the diaminooxidase is provided substantially in its active form, which means that enzymes which, for instance, do not comprise copper in their prosthetic group and do not at least exhibit wild-type activity, are not suitable for the applications according to the invention.

The pharmaceutical composition according to the invention comprises a pharmaceutical form which allows for an administration selected from the group consisting of epidermal, oral, peroral and sublingual administration. The epidermal administration of DAO is primarily advantageous in case of histamine-induced diseases, or conditions, respectively, at the surface of the skin, or on the outermost layers of the skin, respectively, since by this it is, e.g., possible to successfully treat allergic reactions that resulted from a contact of the skin with an allergen. Likewise itching, caused in various diseases, like urticaria, atopic eczema and the like, triggered by a release of histamine, can be stopped. By the oral and peroral administration of the compositions according to the invention it is possible to get DAO into the gastro-intestinal tract of an individual and to successfully stop, or treat, respectively, the histamine-induced illnesses there by degrading histamine. The range of activity of the DAO is mainly restricted to the gastrointestinal tract since the high acid content in the stomach has a negative effect on the activity of DAO. Therefore, when administering DAO orally or perorally, it is necessary to protect DAO from gastric acid until it has reached the intestinal tract. However, if DAO is administered sublingually, the enzyme is quickly taken up in the mouth by the oral mucosa and delivered into the bloodstream. In this way it is possible to quickly and easily transfer DAO into the bloodstream without having to transport the enzyme intravenously or having to transport it through the stomach to the intestines without any harm, which delays a rapid start of the enzyme effect.

The pharmaceutical composition is provided in a form of administration selected from the group consisting of hydrogel, gastric-juice-resistant pellet, drops, in particular eye drops and nose drops, tablets and capsules. According to the present invention, it is possible to convert DAO by processing methods according to those known in the prior art into pharmaceutical forms to be administered. Therefore, pharmaceutical compositions comprising DAO also contain further ingredients which are used to stabilize the enzyme, on the one hand, and to bring the enzyme into the corresponding galenic form, on the other hand. DAO may, of course, also be administered together with other pharmaceutically active substances in a single form of administration, or separately, as long as the enzyme is not inhibited by any one of these active substances such that an activity of the enzyme does not unfold its desired effect.

The DAO comprising hydrogel compositions according to the invention preferably have a viscosity of from 0.5 to 5 cp (centipoise), more preferably from 1 to 2 cp, in particular 1.1 to 1.6 cp, at a shearing speed of 41 sec−1, wherein the measurement may be effected by means of viscosimeters known in the prior art. It has been found that the DAO-containing hydrogel composition has advantageous properties (e.g. topic distributing ability, good handling) particularly in these viscosity ranges. At a lower viscosity of 0.5 cp, the hydrogel composition proved to be too thin in order to allow for a user-friendly handling of the preparation. Preferably, polyacrylates (e.g. CARBOPOL (polyacrylic acid), cellulose derivatives, or modified cellulose, respectively, in particular hydroxy ethylcellulose (e.g. NATROSOL (water soluble hydroxyethylcellulose), methylcellulose, hydroxypropylmethyl cellulose and hydroxymethylcellulose, starch and modified starch, natural and synthetic rubbers, such as, e.g., tragacanth, guar, Carrageenan, gelatine, sodium alginate, PVP, polyvinyl alcohol and mixtures thereof are used as gelatinizing agents. As gelatinizing agent, particularly preferably, hydroxyethyl cellulose (e.g. NATROSOL (water soluble hydroxyethylcellulose) is used, wherein, in particular, NATROSOL (water soluble hydroxyethylcellulose) Type 250 HHR exhibits a particularly good stability already at a low concentration. The pH of the hydrogel composition preferably ranges from 7.0 to 9.0, preferably from 7.2 to 8.5, more preferably from 7.5 to 8.0. This pH range is preferably adjusted with a buffer, in particular with a Bis/Tris buffer, wherein further salts (e.g. 20-300 mM, preferably from 50 to 200 mM, in particular 100 mM, NaCl) may be added for maintaining the DAO enzyme activity and stability. If the total concentration of the salts is below 20 mM, the DAO has a poorer stability which may lead to a loss of activity.

Furthermore, also preservatives may be added to the hydrogel composition according to the invention, which preservatives substantially prevent the proliferation of microorganisms in the composition. What is important here is to choose the preservatives such that the antimicrobial substances do not inhibit the DAO activity in a manner that its enzyme activity does no longer suffice to achieve the object of the present invention (degradation of histamine). By activity tests which are carried out with DAO and the preservative, such substances can be identified. Preferably, chlorhexidin, parabens (para-hydroxy-benzoic acid esters, in particular butyl, ethyl, methyl or propyl parabens), benzoates (e.g. Na-benzoate), sorbates (e.g. K-sorbate) carbamates (e.g. iodopropynyl butyl carbamate) and combinations thereof (e.g. ROKONSAL mixture of Na-benzoate, K-sorbate and iodopropynyl-butyl-carbamate) are used as preservative. Particularly preferred are hydrogel compositions which comprise NATROSOL (water soluble hydroxyethyl-cellulose) as gelatinizing agent and ROKONSAL (a combination of sodium-benzoate, potassium-sorbate and iodopropynyl-butyl-carbamate) and/or parabens as preservatives. Of course, according to the invention also scents and aromatic substances which are employed in the cosmetics industry, e.g., can be added.

A further aspect of the present invention relates to a food supplement composition, or to a dietary foodstuff (DFS) which is adapted as a gastric-juice-resistant pellet, drops or infusion. The oral administration of DAO by means of a food, a food supplement, or a dietary foodstuff requires this enzyme to get into that part of the body in which it is to unfold its activity. Since histamine plays an important role in the intestinal tract, it is necessary for the DAO to be adapted or provided in a manner that it can pass the highly acid-containing stomach unharmed. In this instance, the DAO preferably is processed to a gastric-acid-resistant pellet.

Since at a pH of below 3, the DAO is irreversibly damaged (the pH in the stomach ranges between pH 2 and 4), in order to transport the DAO through the stomach into the intestinal tract it is necessary for the DAO to be provided in an appropriate form of administration (pharmaceutical composition or food supplement composition, or dietary foodstuff, respectively). According to the invention, capsules (e.g. gelatine capsules) and, in particular, gastric juice-resistant pellets have proven particularly advantageous. It is an advantage if the activity of the DAO starts 15 minutes at the latest, preferably 20 minutes at the latest, in particular 30 minutes at the latest, after having been administered.

According to the invention, "gastric-acid-resistant" is to denote that property of the pellet which is capable of protecting an active substance (e.g. DAO) contained therein under the action of a gastric juice, or of a solution having properties comparable to those of gastric juice (e.g. acid) for a certain period of time of at least 10, preferably at least 20, more preferably at least 30, in particular at least 60 minutes such that the active substance undergoes a loss of activity of 50% at the most, preferably 40% at the most, more preferably 30% at the most, most preferred 20% at the most, in particular 10% at the most.

Preferably, after 20 minutes, in particular after 30 minutes, the pellet according to the invention releases in the intestines at least 60%, in particular at least 80% of the DAO activity which was used to formulate the pellets.

Gastric-juice-resistant pellets are pellets which are coated by a gastric-juice-resistant coating, which dissolves at a pH as is found in the intestinal tract. This means that such coatings preferably dissolve at a pH of 4 at the least and 10 at the most. EUDRAGIT (anionic polymer based on methyl acrylate, methyl methacrylate and methacrylic acid), e.g., a gastric-juice-resistant coating based on anionic polymers of methacrylic acid and methacrylates, contains —COOH as functional group and dissolves in the range of pH 5.5 to pH 7. As an alternative to EUDRAGIT (anionic polymer based on methyl acrylate, methyl methacrylate and methacrylic acid), shellac or acetylated starch (e.g. AMPRAC (acetylated starch) 01) may be employed. Since the gastric-juice-resistant coatings known in the prior art have different properties (e.g. pH, at which the coating dissolves, dissolution rate), the materials of the coatings can also be combined. Shellac, e.g., exhibits a good acid resistance, yet it dissolves very slowly in the intestinal tract. AMPRAC (acetylated starch) 01, on the other hand, dissolves rapidly in the intestinal environment, yet it is not sufficiently acid-resistant. In order to compensate the disadvantages of a material, the two above-mentioned materials may, e.g., be mixed at a weight ratio of 60-95/40-5, preferably of 70-90/30-10, shellac/AMPRAC (acetylated starch) 01. A further parameter which has an influence on the release rate of the active substance is the layer thickness of the gastric-juice-resistant pellet. The layer thickness, expressed as mass ratio, is preferably 5 to 30%, more preferably 10 to 20%, of the total mass of the final product. The pellets preferably have an average diameter of from 0.5 to 5 mm, in particular of from 0.7 to 2 mm. Such a size has the advantage that the pellets can quickly pass the stomach.

Preparation of the pellets of the invention which may be used both in the inventive pharmaceutical composition and in the inventive food supplement composition, or dietary foodstuff, respectively, preferably is effected by means of an extruder which requires a thermal stability of the ingredients of the composition, in particular of the active substance DAO, of up to 60° C. (Stricker Arzneiformenentwicklung, Springer Verlag 2003). The pellets may comprise additional pharmaceutical additives in addition to a gastric-juice-resistant coating and DAO. For instance, microcrystalline cellulose (AVICEL (partly hydrolysed microcrystalline cellulose), e.g.) serves as a filler and swelling agent. Cellulose is insoluble in water, and in this form has both crystalline and also amorphous portions. This combination causes a plastic deformability, which means that at a sufficiently high force, an irreversible change in shape will occur. This is a substantial prerequisite for pelletizing in an extruder and spheronizer. During the moist granulation, the microcrystalline cellulose absorbs large amounts of water and by this becomes a readily compressible, coherent mass, also without addition of a binder. According to the invention, the amount of microcrystalline cellulose in a pellet may range between 5 and 70%, preferably between 10 and 60%, even more preferred between 15 and 50%. As the binder or filler, sucrose may be used. Sucrose increases the solubility of the matrix and thus assists in the rapid release of the enzyme. According to the invention, sucrose may be added to a pellet in an amount from 1 to 40%, preferably 5 to 35%, even more preferably 10 to 30%. Hydroxypropyl cellulose (admixed in an amount of preferably 0.5 to 10%) can also be added as a binder and serves for preventing fine dust. Moreover, hydroxypropyl cellulose increases the strength of the pellet and, thus, again contributes to improving the yield. Corn starch can be added to the pellet according to the invention as a filler and disintegrating agent (in a preferred amount of from 1 to 30%). Being a water-insoluble substance, starch can absorb a lot of water and, thus, is an ideal disintegrating agent. Crosscarmellose (Na-CMC; AC-DI-SOL (acetic acid-2,3,4,5,6-pentahydroxyhexanal; sodium) is a pure disintegrating agent which, preferably, can be used in an amount of between 1% and 5%. Too high a portion of AC-DI-SOL (acetic acid-2,3,4,5,6-pentahydroxyhexanal; sodium) will lead to an early disintegration of the pellet already during rounding thereof and, thus, is counterproductive. Crosspovidon, a cross-linked PVP, likewise is water-insoluble and also serves as a disintegrating agent. Due to its polymeric properties, it assists in an improved rounding during the production of pellets (may preferably be admixed in an amount of from 0.5 to 10%). Povidon is a water-soluble additive and serves as a binder. The combination of these different fillers, disintegrating agents and binders leads to a molecular-disperse distribution of the DAO in the pellet and ensures a rapid bioavailability.

Between the gastric-juice-resistant coating and the pellet with the active agent, an insulating layer made of glycerol and/or talcum may be provided. Glycerol serves as a humectant so as to prevent a dehydrogenation and, thus, inactivation of the enzyme.

As an alternative to pellets, the DAO may also be transported in capsules through the stomach into the intestinal tract. Suitable capsules are, e.g., gelatine capsules or starch capsules. The capsules may also contain the pellets according to the invention.

A further aspect of the present invention relates to a cosmetic composition comprising diaminooxidase, which is provided in a cosmetic administration form, in particular as a hydrogel, ointment, spray or as drops. In case of an increased histamine release, or in case of a contact with allergenic substances (e.g. in case of contact allergies or neurodermatitis) body reactions may occur at visible sites of the body, which reactions can be suppressed by administering DAO in cosmetic compositions. Cosmetic compositions comprising DAO may, furthermore, comprise other ingredients known in the prior art, which are used in the preparation of cosmetic products. Hydrogel-comprising cosmetic compositions have substantially the same properties and contain substantially the same ingredients as hydrogels of a pharmaceutical composition according to the invention.

Preferably, the diaminooxidase used in the compositions according to the invention is of non-plant origin.

The use of DAO of non-plant origin in pharmaceutical and cosmetic compositions as well as in food supplements and in dietary foodstuffs has the advantage that allergens occurring in plants will not negatively affect the administration of DAO, since allergens substantially promote the endogenous histamine release. It has been known that primarily plant substances are responsible for histamine-induced diseases. The complete removal of allergy-triggering ingredients from a DAO preparation of plant origin is possible only with a high preparative effort, whereas the DAO according to the invention which is of non-plant origin is completely free from such plant allergens.

According to the present invention, by "non-plant origin" all the DAOs are comprised which are not recovered from plants, but from animal organisms or from other non-plant organisms. Moreover, according to the invention this definition includes all the DAOs which are recombinantly prepared in cell cultures (animal, bacterial, yeasts and the like), or in non-plant organisms of any type, wherein the DNA for the recombinantly prepared DAO is isolated from plant and/or animal organisms by methods known in the prior art, and cloned and expressed in expression systems.

Preferably, all the compositions disclosed in the present invention comprise diaminooxidase of animal origin. By using animal DAO, it is possible to provide the human, or animal body, respectively, with an enzyme which is very similar to the enzyme produced by these individuals themselves in terms of glycosylation, activity and specificity of the DAO produced by these individuals themselves. Moreover, it is possible to entirely exclude plant allergens from the production of DAO.

Preferably, the diaminooxidase is recovered from porcine kidneys. Porcine kidneys are primarily characterized by their high content of DAO. From porcine kidneys, the enzyme can be isolated in a simple manner by methods known in the prior art.

According to a further preferred embodiment, the compositions according to the invention comprise diaminooxidase of recombinant origin. By the recombinant production of DAO it is possible to produce large amounts of enzyme and to purify this enzyme in a high yield.

Preferably, the recombinant diaminooxidase is expressed in prokaryotic, preferably in bacterial, or in eukaryotic, preferably in animal or yeast cell cultures and isolated from the expression systems indicated above. Purification of DAO produced by means of these expression systems, which is either expressed in the cells or is secreted from the cells during the expression, is effected by methods known in the prior art. In doing so, it is also possible to provide the DAO with a peptide (e.g. His-tag), polypeptide or protein sequence (e.g. GST-tag) so as to simplify said purification. The recombinant DAO may furthermore be modified by genetic engineering methods such that the enzyme activity of this DAO surpasses the enzyme activity of the wild-type DAO.

A further aspect of the present invention relates to the use of the diaminoxidase according to the invention for producing a medicament for the treatment of histamine-induced clinical pictures. DAO is known to be responsible for the degradation of histamine in the human and animal body. Since histamine-induced diseases are caused by an excess of histamine which is due to a lack of diaminooxidase or to the inhibition of DAO, or by a histamine excess which, as a rule, may be caused by food or also by further extrinsic factors, such as, e.g., contact with allergens, the administration of DAO of the invention lends itself to the treatment of these diseases, or clinical pictures, respectively.

A further aspect of the present invention relates to the use of the diaminooxidase of the invention for producing a medicament for the treatment of urticaria, in particular of chronic and acute urticaria. With urticaria, a release of histamine causes a widening of venoles and an excessive permeability of the capillaries with a resultant oedema. By administering DAO to the affected skin zones it is possible to degrade the histamine at the affected sites and to thereby stop the itching of the urticaria.

A further aspect of the present invention relates to the use of diaminooxidase of the invention for producing a medicament for the treatment of contact allergies. Contact allergies are caused by substances (allergens) which trigger allergic reactions by penetrating into the skin. In order to degrade the histamines released by this contact and thus, stop, or alleviate, respectively, the histamine-induced clinical pictures, DAO is administered.

According to a further aspect of the present invention, a diaminooxidase according to the invention is used for producing a medicament for the treatment of atopic dermatitis. Atopic dermatitis, also known by the name neurodermatitis, is a frequent skin disease associated with pronounced itching, occurring mostly in children and in young adults. The cause of this itching is the excessive release of histamines at the affected sites of the skin. Also in this case, DAO can attribute to the reduction of histamines in these areas and, thus, alleviate, or prevent, respectively, the symptoms of atopic dermatitis.

According to a further aspect, the present invention relates to the use of the diaminooxidase of the invention for producing a medicament for the treatment of scombrotoxism. Scombrotoxism is a histamine poisoning after the consumption of mackerel varieties, e.g. of tuna. When interrupting the cold chain, or when delaying preparation, so-called scombrotoxins form in scombrides, which lead to a histamine enrichment. The consequences of this histamine poisoning are i.a. fever, nausea, vomiting, bellyache, and urticaria. In this case, DAO can be used as a detoxicating agent.

A further aspect of the present invention relates to the use of the diaminooxidase of the invention for producing a medicament or a food supplement, or for a dietary foodstuff, for removing histamine from the gastro-intestinal tract, or reducing it therein, respectively.

The reduction of histamine in the intestinal tract is of particular importance in case of an increased supply of histamine (exogenic supply, e.g. by food) to the body of an individual, or if, e.g., the activity of the DAO in the intestinal tract is partially or entirely inhibited, or not provided at all, respectively. The medicament, or food supplement, or dietary foodstuff, respectively, of the invention thus serves for supplying enzymatically active DAO which contributes to the degradation of histamine in the intestinal tract.

A further aspect of the present invention relates to the use of diaminooxidase for producing a medicament for removing histamine from the bronchial system.

The intake of histamine-releasing substances, such as, e.g., pollen, into the bronchial system, or into the lungs, respectively, can lead to pronounced allergic reactions. In order to degrade the released histamine, the DAO of the invention may, e.g., be introduced into the bronchial system, or into the lungs, respectively, by inhalation sprays and the like.

The invention will be further explained by the following examples without, however, being restricted thereto.

EXAMPLES

Example 1

DAO was actively stabilized in a cellulose-based pellet, and the pellet was coated with a gastric-juice-resistant coating. In the dissolution test, it could be shown that more than 70% of the activity are released into the surroundings within the first hour.

Example 2

Furthermore, the enzyme was stabilized in a hydrogel. Storage at room temperature and at 37° C. did not show a decrease in the activity within 4 months. Occurring vesicles and itching of the skin after stimulation with histamine disappeared a few minutes after application of the hydrogel.

Example 3

DAO stabilized in the hydrogel was tested on a total of 13 persons. By way of a questionnaire it was distinguished between stress by contact allergy (n=5), neurodermatitis/dermatoses (n=6) and insect bites (n=2). In all patients with contact allergies and in neurodermatitis patients, a positive effect was attested; in case of insect bites, 50% of the volunteers could report a positive effect.

| Stress | Positive Effect/Number of Volunteers |
| --- | --- |
| Neurodermatitis/Dermatosis | 6/6 |
| Contact allergy | 5/5 |
| Insect bite | 1/2 |

The effect of the hydrogel occurred within the first 10 minutes, the effect on an average lasting for more than one hour.

| | 0-10 min | 10-30 min | 30-60 min | >1 h | >3 h |
| --- | --- | --- | --- | --- | --- |
| Start of effect | 11 | 1 | | | |
| Duration of effect | | 3 | 1 | 2 | 6 |

No volunteer reported uncomfortable effects in case of a repeated application.

Two neurodermatitis patients stated that the hydrogel of the invention was more effective than a cortisone ointment used at that time.

Example 4

Gastric-juice-resistant pellets were prepared with 3% of DAO which had an initial activity of 80,000 U/ml, 40% of microcrystalline cellulose, 20% of sucrose, 22% of other binders, fillers and disintegrating agents and with 15% of a gastric-juice-resistant coating. The release of DAO from the pellets was observed for a period of 180 minutes by means of an activity assay. Here, in the solution in which the pellets had been dissolved, already after 10 minutes a DAO activity of 40%, after 30 minutes an activity of 70%, after 60 minutes an activity of 80% and after 180 minutes an activity of 100% of the DAO amount originally employed was detected. The activity measurement of the DAO was as described in AT 411688, wherein, however, also other known methods could very well be employed for measuring the enzyme activity.

REFERENCES

Bachrach U., in: B. Mondovi (Ed) (1985), Structure and Functions of Amine Oxidase, CRC Press, Boca Raton, pp. 5-20x Bartholomew M. J. et al (1990), Cancer 66:1539-1543

James S. M., Palcic M. M., Scaman C. H., Smith A. J., Brown D. E., Dooley D. M., Mure M., Klinman J. P. (1992), Biochemistry 31:12147-12154

James S. M., Mu D., Wemmer D., Smith A. J., Kaur S., Maltby D., Burlingame A. L., Klinman J. P. (1990), Science 248:981-987

Keskinege A., Elgun S., Yilmaz E. (2001), Biochim. Biophys. Acta 25:76

Kitanaka J., Kitanaka N., Tsujimura T., Terada N., Takemura M. (2002), European Journal of Pharmacology 437:179-185

Kluetz M. D., Schmidt P. G. (1977), Biochem. Biophys. Res. Comm. 76:40-45

Küfner M. A., Ulrich P., Raithel M., Schwelberger H. G. (2001), Inflamm. res. 50, Supplement 2, 96-97

Kusche J., Menningen R., Leisten L., Krakamp B. (1988), Adv. Exp. Med. Biol. 250:745-52

Kusche J., Bieganski T., Hesterberg R., Stahlknecht C. D., Feussner K. D., Stahlenberg I., Lorenz W. (1980), Agents Actions 10:110-3

Mennigen R, Bieganski T, Elbers A, Kusche J (1989), J. Chromatogr. B Biomed. Sci. Appl. 27:221

Mizuguchi H., Imamura I., Takemura M., Fukui H. (1994), J. Biochem. 116:631-635

Mu D., James S. M., Smith A. J., Brown D. E., Dooley D. M., Klinman J. P. (1992), J. Biol. Chem. 267:7979-7982

Nilsson B. O., Kockum I., Rosengren E. (1996), Inflammation Res. 45:513-518

Rinaldi A., Vecchini P., Floris G. (1982), Prep. Biochem. 12:11-28

Shah M. A., Ali R. (1988), Biochem. J. 253:103-107

Taylor S. L. (1986), Crit. Rev. Toxicol. 17:91-128

The invention claimed is:

1. A pharmaceutical composition for reducing histamine in the gastro-intestinal tract of a person, said composition comprising a gastric-juice-resistant pellet comprising an effective amount of diaminooxidase to reduce histamine in the gastro-intestinal tract of a person, wherein the pharmaceutical composition is formulated for oral administration, and wherein the gastric juice-resistant pellets comprises 10 to 20% gastric-juice resistant coating.

2. The pharmaceutical composition of claim 1, wherein said composition is a food supplement composition.

3. The pharmaceutical composition of claim 1, wherein said composition is a dietary foodstuff.

4. The pharmaceutical composition of claim 1, wherein said diaminooxidase is a diaminooxidase of non-plant origin.

5. The pharmaceutical composition of claim 4, wherein said diaminooxidase is of animal origin.

6. The pharmaceutical composition of claim 5, wherein said diaminooxidase of animal origin is derived from porcine kidney.

7. The pharmaceutical composition of claim 1, wherein said diaminooxidase is of recombinant origin.

8. The pharmaceutical composition of claim 7, wherein said diaminooxidase of recombinant origin is recovered from one of prokaryotic and eukaryotic cell cultures.

9. The pharmaceutical composition of claim 8, wherein said prokaryotic cell cultures are bacterial cell cultures.

10. The pharmaceutical composition of claim 8, wherein said eukaryotic cell cultures are selected from the group consisting of animal and yeast cell cultures.

11. The pharmaceutical composition of claim 1, wherein the gastric juice resistant pellets comprise anionic polymers of methacrylic acid and methacrylates, shellac, acetylated starch, or a combination thereof.

12. The pharmaceutical composition of claim 1, wherein the gastric-juice resistant pellets comprise microcrystalline cellulose.

13. The pharmaceutical composition of claim 1, wherein the gastric-juice resistant pellets have an average diameter of 0.7 to 2 millimeters.

14. The pharmaceutical composition of claim 1, wherein the gastric-juice resistant pellets comprise by weight 3% of diaminooxidase which had an initial activity of approximately 80,000 U/ml, 40% microcrystalline cellulose, and 20% sucrose, and 15% gastric-juice resistant coating.

15. The pharmaceutical composition of claim 1, wherein the gastric juice-resistant pellet is capable of protecting an active substance under the action of a gastric juice for at least 10 minutes, wherein the active substance undergoes a loss of activity of no more than 50%.

16. The pharmaceutical composition of claim 1, wherein the diaminooxidase had an initial activity of approximately 80,000 U/ml.

17. The pharmaceutical composition of claim 1, wherein the gastric juice-resistant pellets comprises 13 to 17% gastric juice resistant coating.

18. The pharmaceutical composition of claim 1, wherein the gastric juice-resistant pellets comprises 15% gastric-juice resistant coating.

* * * * *